United States Patent [19]

Perrault et al.

[11] Patent Number: 5,264,249
[45] Date of Patent: Nov. 23, 1993

[54] METHOD FOR MAKING A CONDUCTIVE COATED PRODUCT

[75] Inventors: James J. Perrault, Brooklyn Center; David D. Verness, Forest Lake; Kevin Seifert, Champlin; C. Bisson, St. Paul, all of Minn.

[73] Assignee: Medtronic, Inc., Minn.

[21] Appl. No.: 854,166

[22] Filed: Mar. 20, 1992

[51] Int. Cl.⁵ .............................................. B05D 1/38
[52] U.S. Cl. .............................. 427/327; 427/388.2; 427/388.4; 427/388.5
[58] Field of Search ................ 427/327, 388.2, 388.4, 427/388.5, 250, 299

[56] References Cited

U.S. PATENT DOCUMENTS

| | | | |
|---|---|---|---|
| 3,984,500 | 10/1976 | Dickie et al. | 427/407 |
| 3,987,127 | 10/1976 | Dickie et al. | 427/250 |
| 3,992,477 | 11/1976 | Dickie et al. | 427/250 |
| 4,228,216 | 10/1980 | Austin et al. | 427/151 |
| 4,391,278 | 7/1983 | Cahalan et al. | . |
| 4,427,766 | 6/1984 | Mohr | . |
| 4,581,821 | 4/1986 | Cahalan et al. | . |

*Primary Examiner*—Anthony McFarlane
*Attorney, Agent, or Firm*—Daniel W. Latham; Harold R. Patton

[57] ABSTRACT

A method for making a conductive coated product comprising the steps of abrading a conductive metal substrate, applying to the conductive metal substrate a layer of a curable composition which includes 2-acrylamido-2-methylpropanesulfonic acid, water and/or alcohol, and a curing agent and curing the composition on the substrate. The resulting product can be used to make medical electrodes and other electrically conductive medical products

22 Claims, 2 Drawing Sheets

METHOD FOR MAKING A CONDUCTIVE COATED PRODUCT

BACKGROUND OF THE INVENTION

This invention relates to the manufacture of an electrically conductive coated product suitable for medical applications and especially to such conductive products having a metal substrate on which a conductive hydrogel polymer layer is formed.

Electrically conductive coated products have been made with an electrically conductive hydrogel which has been cured on the surface of an metal substrate such as in U.S. Pat. Nos. 4,391,278 and 4,581,821 issued to Cahalan et al. Laminated conductive products can be purchased in roll form from the Promeon Division of Medtronic, Inc. For example, a product designated RG-51 is a product which includes three layers. A first layer is an aluminum/polyester laminate; a second layer is a hydrogel based on 2-acrylamido-2-methylpropanesulfonic acid; and a third layer is a release liner. It was noted that in the conventional process for producing this product, localized corrosion of the aluminum substrate occurred after the product was made. The result was unacceptable pitting of the substrate and a high scrap rate for the finished product.

It would therefore be desirable to provide an improved process for making metal/hydrogel products by which the corrosion of the finished product is prevented.

BRIEF DESCRIPTION OF THE INVENTION

This and other objects have been accomplished by the present invention. We have discovered a method for making a conductive coated product comprising the steps of abrading a conductive metal substrate, applying to the conductive metal substrate a layer of a curable composition which includes 2-acrylamido-2-methylpropanesulfonic acid, water and/or alcohol, and a curing agent and curing the composition on the substrate. We have also discovered that when a metal substrate is coated with a layer of a curable composition which includes 2-acrylamido-2-methylpropanesulfonic acid, water and/or alcohol, and a ultraviolet sensitive curing agent and the composition is then cured on the substrate, the application of a heat treatment to the cured coating and substrate can also reduce the incidence of corrosion on the finished product. Preferably, these two methods are combined to provide a product free of visible corrosion.

DESCRIPTION OF THE PREFERRED EMBODIMENTS

Figure 1:
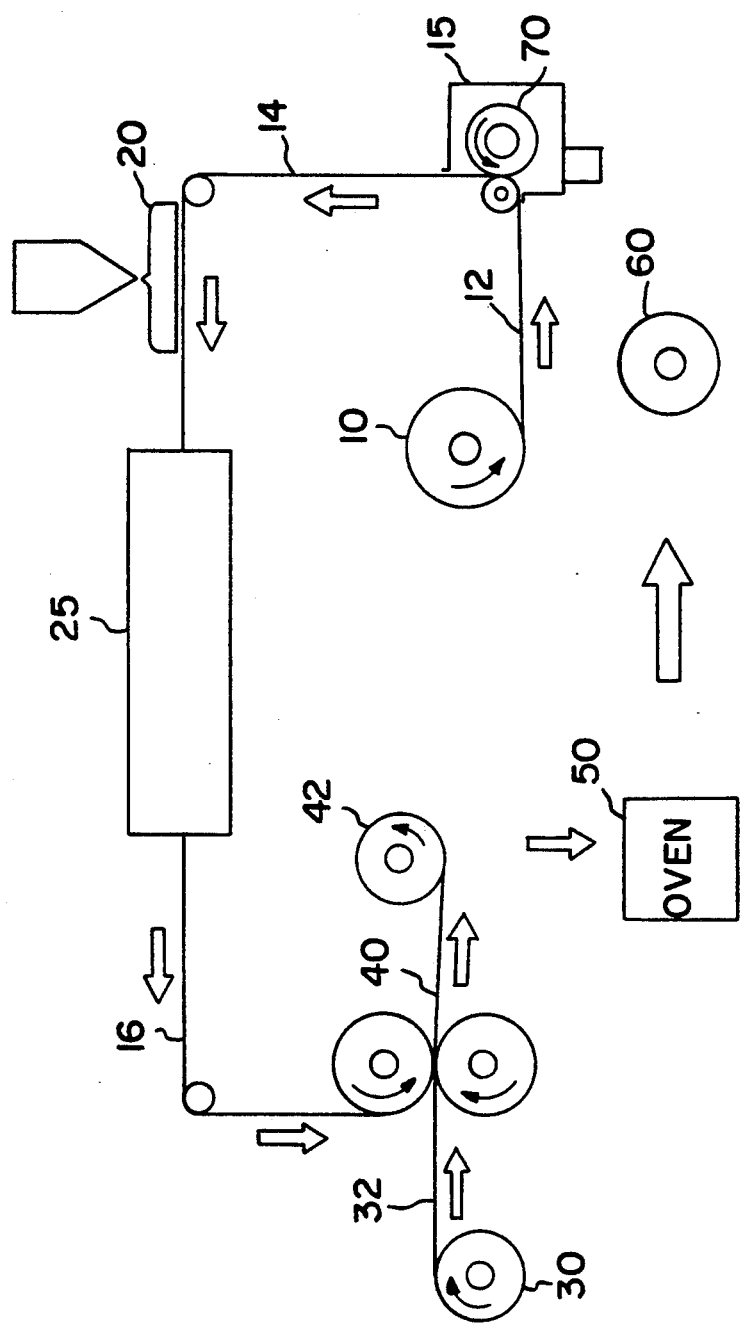
FIG. 1 is a schematic representation of the method according to the present invention.

Referring to FIG. 1, the method of making a conductive coated product is shown schematically. Metal substrate material in roll form 10 is unwound in a web 12 which passes through an abrading station 15 which produces an abraded substrate 14, a coating station 20 which adds a layer of uncured hydrogel material onto the abraded substrate 14, and a curing station 25 which cures the hydrogel material. Release liner material in roll form 30 is unwound in a web 32 and is joined with the web with cured coating 16. The resulting laminate 40 is wound into a roll 42. The roll 42 is placed into an oven 50 where it is heated to form a finished roll product 60.

Figure 2:
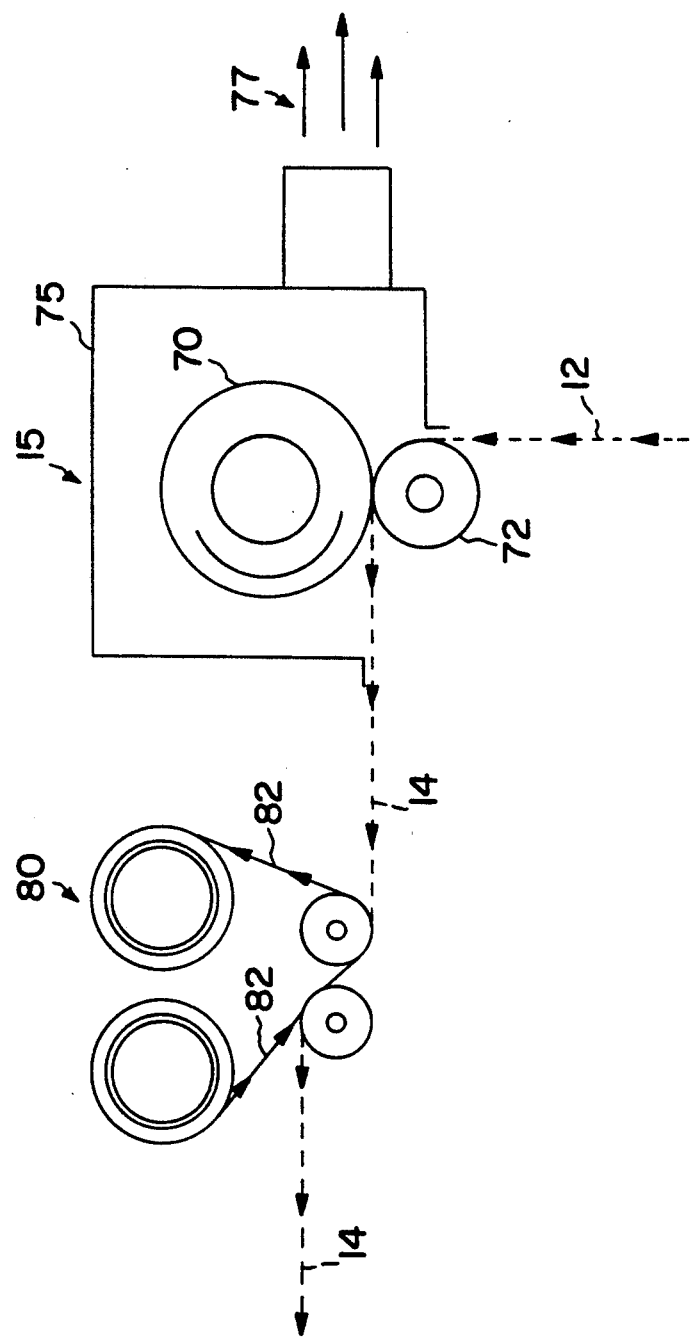
FIG. 2 is an expanded schematic representation of the abrading station of FIG. 1 together with optional means for removing particulate residue.

The metal substrate material 10 is typically a thin foil of metal laminated on a polymeric backing material. A polyester backing material such as a polyester terephthalate film with a thin coating (e.g. 0.001 inch) of aluminum or tin on one side can be used. The metal substrate material 10 used is substantially free of rolling oil and other contaminants. The metal substrate material 10 extends as a web 12 to an abrading station 15 where the metal side of the web 12 is mildly abraded to provide a microscopically rough surface. The abrasions are preferably less than 25 $\mu$m apart and between about 2 $\mu$m and 10 $\mu$m in depth and more preferably, between about 2 $\mu$m and 20 $\mu$m apart and between about 3 $\mu$m and 6 $\mu$m apart. The abrasions are preferably aligned predominantly in the same direction as the direction of travel for the web 12. Referring now also to FIG. 2, the abrasions can be produced by an abrasion wheel 70 such as an ultra fine silica carbide flap brush (e.g. 3M Company Scotch-Brite ® Finishing Flap Brush Grade ULF). The metal substrate 12 is drawn between a backup roll 72 and the counter-rotating abrasion wheel 70. It will be appreciated by those skilled in the art that the degree and uniformity of abrasion is controlled by the combination of the speed of the web 12, the pressure applied between the abrasion wheel 70 and the backup roll 72, and the rotational speed of the abrasion wheel 70. In a preferred embodiment of the invention, the abraded substrate 14 is also cleaned to prevent stray particles from marring the appearance of the finished product 60. Cleaning can be accomplished, for example, by providing a housing 75 enclosing the abrasion wheel 70 and the abraded substrate 14 and attaching a vacuum source 77 to the housing 75 whereby particles released by the abrasion process can be swept away. In yet another method for cleaning a separate cleaning station 80 can be optionally employed in which a web 82 of paper or cloth is pressed against the abraded substrate 14 and moved in a direction opposite to the direction of movement of the abraded substrate 14.

Although the abrasion station 15 is shown to be a part of a continuous production system, it has also been found that it is possible to abrade the metal substrate material 10 in a separate operation, store the abraded substrate for a desired period of time and then apply a coating to the pre-abraded material to make the product 60 without again abrading the substrate.

The coating station 20 adds a layer of uncured hydrogel material to the abraded surface of the substrate 14. The uncured hydrogel material is a mixture of 2-acrylamido-2-methylpropanesulfonic acid (AMPS) or one of its salts, copolymers of the acid, copolymers of the salts of the acid and their various mixtures with water and/or an alcohol. Such compositions are set forth more fully in U.S. Pat. Nos. 4,391,278 and 4,581,821 issued to Cahalan et al. which are incorporated herein by reference. The compositions can include a variety of additives and modifiers including humectants such as glycerol or propylene glycol, thickeners such as polyvinylpyrrolidone or polyvinyl alcohol, monomers such as acrylic acid or acrylamide, crosslinking agents such as methylene-bis-acrylamide, fillers such as silica, ionizable metal salts such as potassium chloride or sodium chloride, pH modifiers such as sodium hydroxide, and various curing agents. A particularly useful curing agent for this process is hydroxycyclohexylphenylketone which can be added to the AMPS and other ingredients in a solution of isopropanol. It produces a cure of the hydrogel coating when it is exposed to ultraviolet light. The uncured hydrogel material can therefore be premixed and applied to the substrate by conventional coating equipment. Preferably, the uncured hydrogel material is handled in an atmosphere that is dry and substantially free of oxygen.

The curing station 25 provides the necessary conditions for the hydrogel coating on the abraded substrate 14 to cure. For example, heat or ultraviolet light can be applied depending on the curing agent used Curing by application of ultraviolet light is preferred. After the hydrogel coating is cured, the release liner material in roll form 30 is unwound in a web 32 and is joined with the web with cured coating 16. The resulting laminate 40 is wound into a roll 42.

If the material has been cured by application of ultraviolet light, the roll 42 then undergoes a heat treatment operation whereby it is placed into an oven 50 at a temperature of at least 45° C. and preferably in the range of about 50°–65° C. for at least 10 hours and preferably for more than 24 hours to make a finished product 60. The time required to accomplish the heat treatment will, of course, depend upon the size of the roll 42 and its heat transfer characteristics. Heat treatment could be accomplished in as little as one hour for a small sample.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. A method for making a conductive coated product comprising the steps of:
   a. abrading a conductive metal substrate;
   b. applying to the abraded metal substrate a layer of a curable composition including:
      1. 2-acrylamido-2-methylpropanesulfonic acid;
      2. a component selected from the group consisting of water, alcohol and mixtures thereof; and
      3. a curing agent; and
   c. curing the composition on the substrate.

2. The method of claim 1 wherein the abrasions are less than 25 μm apart.

3. The method of claim 1 wherein the abrasions are in the range of a 2 μm to 10 μm in depth.

4. The method of claim 1 wherein the curable composition is continuously coated on a web of metal substrate.

5. The method of claim 4 wherein the abrasions are aligned in the same direction as the direction of travel for the web of metal substrate.

6. The method of claim 1 wherein the curable composition also comprises a humectant selected from the group consisting of propylene glycol, glycerol and mixtures thereof.

7. The method of claim 1 wherein the curable composition also comprises a monomers selected from the group consisting of acrylic acid, acrylamide and mixtures thereof.

8. The method of claim 1 wherein the curable composition also comprises methylene-bis-acrylamide.

9. The method of claim wherein the curing agent is hydroxycyclohexylphenylketone.

10. A method for making a conductive coated product comprising the steps of:
    a. applying to a conductive metal substrate a layer of a curable composition including:
       1. 2-acrylamido-2-methylpropanesulfonic acid;
       2. a second component selected from the group consisting of water, alcohol and mixtures thereof; and
       3. a curing agent which is activated by ultraviolet light;
    b. curing the composition on the substrate by applying ultraviolet light; and
    c. heating the cured composition and substrate at a temperature of at least 45° C.

11. The method of claim 10 wherein the cured composition and substrate are heated for at least one hour.

12. The method of claim 10 wherein the cured composition and substrate are heated for at least ten hours.

13. The method of claim 10 wherein the curable composition is continuously coated on a web of metal substrate.

14. The method of claim 10 wherein the curable composition also comprises a humectant selected from the group consisting of propylene glycol, glycerol and mixtures thereof.

15. The method of claim 10 wherein the curable composition also comprises a monomers selected from the group consisting of acrylic acid, acrylamide and mixtures thereof.

16. The method of claim 10 wherein the curable composition also comprises methylene-bis-acrylamide.

17. The method of claim 10 wherein the curing agent is hydroxycyclohexylphenylketone.

18. A method for making a conductive coated product comprising the steps of:
    a. abrading a conductive metal substrate;
    b. applying to the abraded metal substrate a layer of a curable composition including:
       1. 2-acrylamido-2-methylpropanesulfonic acid;
       2. a component selected from the group consisting of water, alcohol and mixtures thereof; and
       3. a curing agent which is activated by ultraviolet light;
    c. curing the composition on the substrate by applying ultraviolet light; and
    d. heating the cured composition and substrate at a temperature of at least 45° C.

19. The method of claim 18 wherein the abrasions are less than 25 μm apart.

20. The method of claim 18 wherein the abrasions are in the range of about 2 μm to 10 μm in depth.

21. The method of claim 18 wherein the cured composition and substrate are heated for at least one hour.

22. The method of claim 18 wherein the cured composition and substrate are heated for at least ten hours.

* * * * *